United States Patent
Vermeiren et al.

(10) Patent No.: US 11,255,604 B2
(45) Date of Patent: Feb. 22, 2022

(54) PROCESS FOR REMOVING LIGHT COMPONENTS FROM AN ETHYLENE STREAM

(71) Applicants: Total Research & Technology Feluy, Seneffe (BE); IFP Energies Nouvelles, Rueil Malmaison (FR)

(72) Inventors: Walter Vermeiren, Houthalen (BE); Catherine Boutrot, Chatou (FR); Manuela Arratia, Paris (FR)

(73) Assignee: Total Research & Technology Feluy, Seneffe (BE)

(*) Notice: Subject to any disclaimer, the term of this patent is extended or adjusted under 35 U.S.C. 154(b) by 60 days.

(21) Appl. No.: 16/106,490

(22) Filed: Aug. 21, 2018

(65) Prior Publication Data

US 2019/0024971 A1  Jan. 24, 2019

Related U.S. Application Data (62) Division of application No. 14/651,441, filed as application No. PCT/EP2013/076609 on Dec. 13, 2013, now Pat. No. 10,101,083.

(30) Foreign Application Priority Data

Dec. 13, 2012 (EP) ................................ 12290437

(51) Int. Cl.
*F25J 3/02* (2006.01)
*C07C 7/09* (2006.01)
(Continued)

(52) U.S. Cl.
CPC ............ *F25J 3/0238* (2013.01); *B01D 3/343* (2013.01); *C07C 1/24* (2013.01); *C07C 7/005* (2013.01);
(Continued)

(58) Field of Classification Search
CPC .. F25J 3/0238; F25J 3/0209; F25J 3/02; F25J 1/0085; F25J 2215/62; C07C 7/04;
(Continued)

(56) References Cited

U.S. PATENT DOCUMENTS 5,233,060 A * 8/1993 Pendergast ........... C07D 301/32
549/523
5,361,589 A * 11/1994 Howard ............... C10G 70/043
62/627
(Continued)

OTHER PUBLICATIONS

Office Action issued in Indian Application 5029/DELNP/2015, dated Aug. 24, 2018, 6 pages.

*Primary Examiner* — Frantz F Jules
*Assistant Examiner* — Webeshet Mengesha
(74) *Attorney, Agent, or Firm* — Albert Shung (57) ABSTRACT

A process for removing light components from an ethylene stream may include providing a dried ethylene stream containing ethylene, ethane, CO, $CO_2$, $H_2$, $CH_4$, and $C_{3+}$ hydrocarbons. The process may include sending the dried ethylene stream to a stripper to produce an overhead stream containing ethylene, CO, $H_2$ and $CH_4$, and a bottom stream containing ethylene, ethane, $CO_2$, and $C_{3+}$ hydrocarbons. The gaseous phase on top of the stripper may be condensed in a heat exchanger cooled by a refrigerant stream to get a first gaseous phase and a first liquid phase. The first gaseous phase may be condensed in a heat exchanger cooled by liquid ethane or liquid ethylene to get a second gaseous phase containing ethylene CO, $H_2$ and $CH_4$ and a second liquid phase. The first and second liquid phases may be the reflux of the stripper.

3 Claims, 4 Drawing Sheets

(51) Int. Cl.
  *B01D 3/34* (2006.01)
  *C07C 7/00* (2006.01)
  *C07C 7/12* (2006.01)
  *C07C 1/24* (2006.01)
  *C07C 7/04* (2006.01)

(52) U.S. Cl.
  CPC ............... *C07C 7/04* (2013.01); *C07C 7/09* (2013.01); *C07C 7/12* (2013.01); *F25J 3/0209* (2013.01)

(58) Field of Classification Search
  CPC .. C07C 7/005; C07C 7/09; C07C 7/12; B01D 3/343; B01D 3/143
  See application file for complete search history.

(56) References Cited

U.S. PATENT DOCUMENTS

| | | | |
|---|---|---|---|
| 5,741,350 A * | 4/1998 | Rowles | B01D 53/1487 95/176 |
| 5,960,643 A * | 10/1999 | Kuechler | C07C 7/005 62/620 |
| 9,079,812 B2 | 7/2015 | Coupard et al. | |
| 2009/0193846 A1* | 8/2009 | Foral | C01B 3/506 62/620 |
| 2011/0172375 A1* | 7/2011 | Yeh | B01J 19/002 526/74 |

\* cited by examiner

PROCESS FOR REMOVING LIGHT COMPONENTS FROM AN ETHYLENE STREAM

CROSS-REFERENCE TO RELATED APPLICATIONS

This application is divisional of U.S. patent application Ser. No. 14/651,441, filed Jun. 11, 2015, which claims the benefit of PCT/EP2013/076609, filed on Dec. 13, 2013, which claims priority from EP 12290437.8, filed on Dec. 13, 2012, which are incorporated by reference in their entireties for all purposes.

FIELD OF THE INVENTION

The present invention is a process for removing light components from an ethylene stream. Optionally oxygenated contaminants are also removed.

Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds. The limited supply and increasing cost of crude oil has prompted the search for alternative processes for producing hydrocarbon products.

Olefins can be produced by dehydration of the corresponding alcohol. Ethanol can be obtained by fermentation of carbohydrates, from the synthesis gas, a mixture of CO and H2 or any other process. Made up of organic matter from living organisms, biomass is the world's leading renewable energy source. The effluent produced by the ethanol dehydration comprises essentially unconverted ethanol, water, ethylene, acetaldehyde as well as light components. Ethanol is removed and can be recycled to the dehydration reactor. It remains a stream comprising essentially ethylene, ethane, CO, CO2, H2, CH4, C3+ hydrocarbons and optionally oxygenates. In an embodiment said stream comprises essentially ethylene, ethane, CO, CO2, H2, CH4, C3+ hydrocarbons as well as up to 1 w % oxygenates. The weight ratio of ethane+CO+CO2+H2+CH4+C3+ hydrocarbons to ethylene is most of time less than 20/80. The removal of the light components, CO, H2 and CH4, may cause a loss of ethylene.

Among oxygenates, acetaldehyde may cause problems in ethylene recovery operations, therefore it would be desirable to remove said oxygenate if any.

BACKGROUND OF THE INVENTION

In the process to produce ethylene the stream to be purified comprising essentially ethylene, ethane, CO, CO2, H2, CH4, C3+ hydrocarbons as well as oxygenates is sent to a stripper (also referred to as a demethanizer) to produce an overhead stream comprising essentially CO, H2 and CH4 and a bottom stream comprising essentially ethylene, oxygenates, ethane, CO2 and C3+ hydrocarbons. Separation of light components depends on their proportion in the stream. If the proportion of light components is relatively high, a very low temperature will be required to separate them from the ethylene stream, and therefore a cold stream will be required.

The following prior arts have already described purification of olefins but they need a caustic wash or a wash column to remove the oxygenates or both.

US 20030098281 A1 describes a method of controlling water and/or oxygenate concentrations of an olefin stream. The method includes contacting the olefin stream with a liquid absorbent. The liquid absorbent is selected from the group consisting of a polyol, amine, amide, nitrile, heterocyclic nitrogen containing compound, and mixtures thereof. A gaseous stream comprising essentially steam, ethylene, propylene and less than 2 w % of oxygenates is condensed in a quench tower. The overhead of said quench tower is washed with a caustic solution to remove CO2 and then contacted with the liquid absorbent to remove the oxygenates.

WO 03 020670 A1 provides a method for removing oxygenated components such as acetaldehyde, CO2 and/or water from an olefin stream. It explains it is desirable to remove such oxygenated components, since they may poison catalysts that are used to further process olefin composition. In addition, the presence of certain oxygenated compounds, such as acetaldehyde, can cause fouling in other olefin purification units, e.g., acid gas treating units. The method comprises providing an olefin stream containing ethylene, propylene, C4+ olefins and acetaldehyde. The olefin stream is separated into a first fraction and a second fraction, wherein the first fraction comprises at least a majority of the ethylene and/or propylene present in the olefin stream, and the second fraction comprises at least a majority of the C4+ olefins and acetaldehyde present in the olefin stream. The first fraction is then acid gas treated by sodium hydroxide or potassium hydroxide. The olefin stream is separated by distillation, preferably, the distillation is extractive distillation using an extractant. The preferred extractant is a polar composition having an average boiling point of at least 38° C. at 1 atm (0.1 MPa). Methanol is one type of preferred extractant.

WO 03 020672 A1 describes method of removing dimethyl ether from an ethylene and/or propylene containing stream. The olefin stream is passed to a water absorption column, methanol is used as the water absorbent. Methanol and entrained water, as well as some oxygenated hydrocarbon, is recovered as the bottoms stream of said water absorption column, an overhead olefin is recovered and sent to a distillation column. The distillation column separates ethylene and propylene, as well as lighter boiling point components from the dimethyl ether and heavier boiling point components, including C4+ components and methanol remaining from the methanol wash. Additional methanol is added to the distillation column to reduce clathrate and/or free water formation in the distillation column. The ethylene and propylene containing stream exits the distillation column as overhead and the heavier boiling point components which include the dimethyl ether and C4+ components exit the distillation column as the bottoms. Ethylene and propylene then flow to a caustic wash column.

WO 03 033438 A1 describes a method for processing an olefin stream containing oxygenates and water, comprising: providing an olefin stream containing oxygenates and water; dewatering the olefin stream; compressing the dewatered olefin stream; washing the olefin stream with methanol to remove at least a portion of the oxygenate from the olefin stream; contacting the methanol washed olefin stream with water; and fractionating the water contacted olefin stream. The recovered olefin stream (washed with methanol and then with water) is further sent to an alkali wash and a drying step. The olefin stream containing oxygenates and water is the effluent of an MTO process.

EP 0 669 389 describes a cryogenic ethylene recovery system in which the ethylene-containing feed gas is cooled and condensed, prior to fractionation. In particular this document describes an improved method which utilizes a combination of one or more partial condensers followed by one or more dephlegmators. In this document, the purification is performed with the help of two demethanizer. The overhead stream of the first demethanizer 117 is passed directly to the second demethanizer 119 without any other treatment.

U.S. Pat. No. 6,444,869 describes a process for the production of ethylene from an oxygenate conversion effluent stream. The oxygenate conversion effluent stream comprises hydrogen, methane, ethylene, ethane, propylene, propane and C4+ olefins. This effluent is compressed, treated to remove oxygenates, passed to a carbon dioxide removal zone wherein carbon dioxide is absorbed by contacting a caustic solution or by contacting an amine solution in combination with a caustic solution in a conventional manner to remove the carbon dioxide, dried, then fractionation is made through a deethanizer and a demethanizer.

US 2005-0283038 A1 described a process for producing an olefins stream from a first vapor effluent stream from an oxygenate to olefin conversion reaction, said first vapor effluent stream comprising C2 and C3 olefins, C4 hydrocarbons, and C2 to C6 carbonyl compounds. In the process, the temperature and pressure of the first vapor effluent stream are adjusted to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more C4 hydrocarbons based upon the total weight of C4 hydrocarbons in the first vapor effluent stream. The second vapor effluent stream is then washed with a liquid alcohol-containing stream to produce a third vapor effluent stream, whereafter the third vapor effluent stream is washed with liquid water to provide a fourth vapor effluent stream comprising the C2 and C3 olefins and about 1.0 wt. % or less C2 to C6 carbonyl compounds. In one embodiment of such a recovery process, at least part of the fourth vapor effluent stream is contacted with a basic component, such as caustic or an amine, to remove the bulk of the carbon dioxide therefrom (thus removing "acid gas" from the fourth vapor effluent stream), whereafter the $CO_2$-depleted stream is dried.

BRIEF SUMMARY OF THE INVENTION

The present invention is a process for removing light components from an ethylene stream comprising:
a) providing a dried ethylene stream (A) comprising essentially ethylene, ethane, CO, CO2, H2, CH4, C3+ hydrocarbons and optionally oxygenates,
b) sending said stream (A) to a stripper (also referred to as a demethanizer) to produce
  an overhead stream comprising essentially ethylene, CO, H2 and CH4,
  a bottom stream comprising essentially ethylene, ethane, CO2, C3+ hydrocarbons and optionally oxygenates, wherein,
the gaseous phase on top of the stripper is condensed in a heat exchanger cooled by a refrigerant stream to get a first gaseous phase and a first liquid phase, in a preferred embodiment the refrigerant stream consists of one or more C3 or C4 hydrocarbons advantageously it consists of liquid and gaseous propane or propylene
the first gaseous phase is condensed in a heat exchanger cooled by liquid ethane or liquid ethylene to get a second gaseous phase referred to as the overhead stream comprising essentially ethylene CO, H2 and CH4 and a second liquid phase,
the first and second liquid phases are the reflux of the stripper.

It has been discovered that when the proportion of the light components in the stream to be purified is low enough the cooling source of the condenser on top of the stripper can be liquid propane or liquid propylene and only a small amount of ethylene escapes with the light components. When the proportion of the light components in the stream to be purified is higher the liquid propane or propylene is not cold enough, a higher part of ethylene escapes with the light components. A colder cooling source is needed. Instead of using a cooling source colder than propane or propylene to condense the whole top of the stripper it has been particularly discovered to maintain the condenser cooled with liquid propane or liquid propylene and insert a subsequent condenser using liquid ethane or liquid ethylene as a cooling source.

Optionally the process of the present invention comprises additional equipment to remove oxygenates, as well as CO2, and get substantially pure ethylene advantageously polymer grade ethylene. In said process there is no caustic wash to remove the CO2 and no wash column to remove the oxygenates.

Said process is referred to as the basic process.

The liquid ethane or liquid ethylene is in fact a mixture of liquid and gas, the refrigerant stream is in fact a mixture of liquid and gas like for instance a mixture of liquid and gaseous of C3 or C4 hydrocarbons. Advantageously it consists of liquid or gaseous propane or propylene.

It would not depart from the invention to use a propane-propylene mixture instead of propane or propylene.

The liquid propane or liquid propylene pressure advantageously ranges from 0.3 to 2 barg (30 kPag to 200 kPag).

The liquid ethane or liquid ethylene pressure advantageously ranges from 0.3 to 5 barg (30 kPag to 500 kPag).

The liquid iso-butane pressure advantageously ranges from 0.3 bara to 0.7 bara (30 kPaa to 70 kPaa).

The gaseous phase condensers on top of the stripper can be arranged in various ways provided that the gaseous phase comprising essentially ethylene CO, H2 and CH4 is cooled by liquid ethane or liquid ethylene before finally leaving the stripper zone.

The condenser cooled by liquid propane or liquid propylene (the first condenser) and the condenser cooled by liquid ethane or liquid ethylene (the second condenser) can be arranged in series, the gaseous phase exiting the first one passing to the second one. They can be arranged in the same shell having two sets of tubes, one for each cooling fluid.

The first condenser can be arranged conventionally with the reflux drum and the second condenser is in the exit of the reflux drum to cool the gaseous phase comprising essentially ethylene CO, H2 and CH4 by liquid ethane or liquid ethylene before finally leaving the stripper zone.

Figure 1:
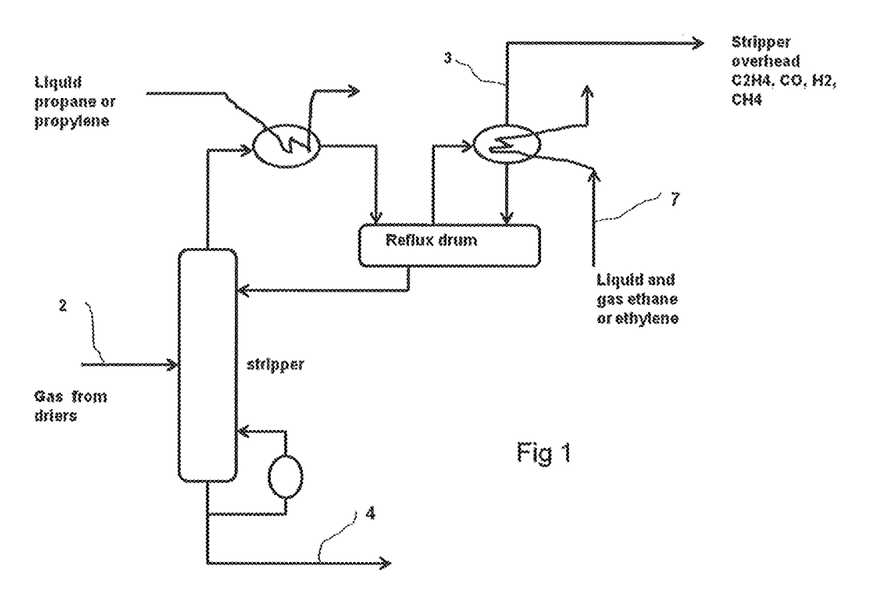
FIG. 1 depicts a flow diagram of a process in accordance with one or more embodiments.

FIG. 1 describes an embodiment of the above process. The dry ethylene stream 2 comprising essentially ethylene, ethane, CO, CO2, H2, CH4, C3+ hydrocarbons and optionally oxygenates is sent to the stripper. A bottom stream 4 comprising essentially ethylene, ethane, CO2, C3+ hydrocarbons and optionally oxygenates is recovered and optionally sent to a further purification. the gaseous phase on top of the stripper is condensed in a heat exchanger cooled by liquid propane or liquid propylene to get a first gaseous phase and a first liquid phase recovered in the reflux drum, the first gaseous phase is condensed in a heat exchanger cooled by liquid ethane or liquid ethylene 7 to get a second gaseous phase 3 referred to as the overhead stream comprising essentially ethylene CO, H2 and CH4 and a second liquid phase recovered in the reflux drum (also known as decanter).

In an embodiment the bottom stream of the stripper comprising essentially ethylene, ethane, CO2, C3+ hydrocarbons and optionally oxygenates is further purified to remove optional oxygenates, as well as CO2, and get substantially pure ethylene advantageously polymer grade ethylene.

Advantageously a part of ethylene is expanded to get liquid ethylene and said liquid ethylene is sent as a cooling fluid to condense the first gaseous phase on top of the stripper. Advantageously ethylene is expanded to a pressure ranging from 0.3 to 5 barg (30 kPag to 500 kPag) to get a cold mixture of gas and liquid.

During the condensation of the first gaseous phase on top of the stripper ethylene returns to gas phase and is advantageously recycled. Should the process of the present invention relates to the production of ethylene by ethanol dehydration said ethylene at low pressure from the condenser can be recycled at any point between the dehydration reactor outlet and the stripper.

In a first embodiment the basic process further comprises (i)
c) sending said bottom stream of step b) to a deethanizer to produce
  a bottom stream comprising essentially ethane, C3+ hydrocarbons and optionally oxygenates,
  an overhead stream consisting essentially of ethylene and CO2,
d) sending said overhead of step c) to a fixed bed CO2 adsorption zone to recover an ethylene stream essentially free of CO2,
or (ii)
c1) sending said bottom stream of step b) to a fixed bed CO2 adsorption zone to recover a stream essentially free of CO2, then sending said stream to a deethanizer to produce
  a bottom stream comprising essentially ethane, C3+ hydrocarbons and optionally oxygenates,
  an overhead stream consisting essentially of ethylene essentially free of CO2.
The above process is referred to as embodiment 1.

Advantageously in said embodiment 1 a part of liquid ethylene in the reflux drum (also known as decanter) of the deethanizer is expanded and sent as a cooling fluid to condense the first gaseous phase on top of the stripper.

In an embodiment the weight ratio of ethane+CO+CO2+H2+CH4+C3+ hydrocarbons to ethylene in (A) is less than 10/90.

In an embodiment the weight ratio of ethane+CO+CO2+H2+CH4+C3+ hydrocarbons to ethylene in (A) is less than 10/90 and above 0.1/99.9.

In an embodiment the weight ratio of ethane+CO+CO2+H2+CH4+C3+ hydrocarbons to ethylene in (A) is less than 5/95.

In an embodiment the proportion of oxygenates in (A) is from 50 wppm to 10000 wppm.

In an embodiment the proportion of oxygenates in (A) is up to 3000 wppm.

In an embodiment the proportion of oxygenates in (A) is up to 2000 wppm.

In an embodiment the proportion of H2 in (A) is up 2 w%

In an embodiment the proportion of H2 in (A) is up 1 w%

In an embodiment the proportion of H2 in (A) is up to 0.5 w%

In an embodiment the proportion of H2 in (A) is up to 0.1 w%

In an embodiment the proportion of CO2 in (A) is up to 400 vol ppm

Advantageously "dried ethylene stream" at step a) means a water content less than 5 wppm, advantageously less than 3 wppm and preferably less than 1 wppm.

In an embodiment when the dried ethylene stream (A) has been made by ethanol dehydration said stream (A) contains substantially no acetylene.

Ethylene treated in accordance with this invention is particularly suitable for use as feedstock for making alpha-olefins, ethylbenzene/styrene, ethyleneoxide/ethyleneglycol, ethylenedichloride and corresponding polymers, like polyethylene homo or copolymer (PE, EPR, EPDM etc), polystyrene (PS), styrene copolymers with butadiene, isoprene, acrylonitrile or combinations (SBS, SIS, SBR, ABS, SAN), polyesters (PET) and polyvinylchlorides (PVC).

In another embodiment, the invention concerns a process for removing light components from an ethylene stream comprising:
a) providing a dried ethylene stream (A) comprising ethylene, ethane, CO, CO2, H2, CH4, C3+ hydrocarbons and optionally oxygenates,
b) separating from said dried ethylene stream (A) in a separation mean being preferably a demethanizer or a stripper
  an overhead gaseous stream (B) comprising ethylene, CO, H2 and CH4,
  a bottom stream (C) comprising ethylene, ethane, CO2, C3+ hydrocarbons and optionally oxygenates, wherein,
c) cooling the overhead gaseous stream (B) to a temperature ranging from −10° C. to −45° C. to get a first gaseous stream (D) and a first liquid stream (E),
d) cooling the first gaseous stream (D) to a temperature ranging from −10° C. to −45° C. lower than the temperature of step c) to get a second gaseous stream (F) comprising ethylene CO, H2 and CH4 and a second liquid stream (G),
e) sending the first and second liquid streams (E) and (G) to said separation mean as a reflux.

In another embodiment said process is remarkable in that cooling of step c) is performed with a refrigerant stream which comprises a mixture of liquid and optionally gaseous hydrocarbons C3 to C4, more preferably liquid and optionally gaseous propane and/or liquid and optionally gaseous propylene with pressure ranging from 30 kPag to 200 kPag.

In another embodiment said process is remarkable in that cooling of step d) is performed with liquid ethane or liquid ethylene at pressure ranging from 30 kPag to 500 kPag.

In another embodiment said process is remarkable in that the bottom stream (C) comprising essentially ethylene, ethane, CO2, C3+ hydrocarbons and optionally oxygenates is further purified to remove oxygenates, as well as CO2, and get substantially pure ethylene stream (H) being preferably a polymer grade ethylene.

In another embodiment said process is remarkable in that part of said substantially pure ethylene stream (H) is expanded, preferably to a pressure ranging from 0.3 to 5 barg (30 kPag to 500 kPag), to get a cold mixture of liquid and of optionally gas, said liquid ethylene is used as refrigerant stream to cool the overhead gaseous stream (B).

In another embodiment said process is remarkable in that during cooling of the overhead gaseous stream (B) the ethylene of the said substantially pure ethylene stream (H) returns to gas phase and is recycled.

In another embodiment, the invention concerns the installation for implementing the processes above:
- a first separator unit, being preferably a demethanizer or a stripper, to separate from stream (A) the overhead gaseous stream (B) and the bottom stream (C)
- a second separator unit, being preferably a reflux drum or a stripper, to separate the first gaseous stream (C) from the first liquid stream (D)
- a first cooling unit, being preferably an heat exchanger, to cool the overhead gaseous stream (B)
- a second cooling unit, being preferably an heat exchanger, to cool the first gaseous stream (C)
- means to convey the dried ethylene stream (A) to the first separator unit, means to convey the overhead gaseous stream (B) to the first cooling unit, means to convey the first gaseous stream (D) to the second cooling unit and means to convey the first and second liquid streams (E) and (G) to said first separator unit All embodiments described above are linked together and should be considered in combination with each other.

DETAILED DESCRIPTION OF THE INVENTION

As regards the oxygenated contaminants also referred to as oxygenates, one can cite, methanol, ethanol, C3 alcohols; ethers such as diethylether and methyl ethyl ether and dimethylether; carboxylic acids such as acetic acid; aldehydes such as acetaldehyde; ketones such as acetone; and esters such as methyl esters; and vinyl derivatives. Particularly problematic oxygenate contaminants in an alcohol dehydration are aldehydes.

As regards the ethylene stream (A) of step a), it can be originating from the dehydration of ethanol. Said dehydration can be made in one or more ethanol dehydration reactors. As regards alcohol dehydration, such process is described in WO-2009-098262, WO-2009-098267, WO-2009-098268 and WO-2009-098269 the content of which is incorporated in the present application. The present invention is very efficient for the purification of ethylene produced by dehydration of ethanol.

The outlet of said dehydration reactor comprises essentially ethylene and steam as well as minor amounts of oxygenates, ethane, CO, CO2, H2, CH4 and C3+ hydrocarbons. "Minor amounts" means the weight ratio of ethane+CO+CO2+H2+CH4+C3+ hydrocarbons to ethylene is less than 20/80 and most of time less than 10/90.

Said outlet of dehydration reactor is initially cooled, typically in a quench tower employing water as the quench medium. In the quench tower, most of the water contained in the outlet of dehydration reactor is condensed and is removed from the bottom of the tower as a liquid water bottom stream. A part of said water bottom stream is cooled in a heat exchanger and recycled as quenching medium to the top of the quench column. The part of the water bottom stream which is not recycled as quenching medium may contain a part of the oxygenates and mostly unconverted ethanol if any. Said stream can be treated in a stripping column to recover a pure water stream. Ethylene, oxygenates, ethane, CO, CO2, H2, CH4 and C3+ hydrocarbons are removed from the top of the quench tower at a pressure typically such as 1 to 16 bars absolute (0.1 MPaa to 1.6 MPaa) and are referred to as the contaminated ethylene stream. Advantageously said contaminated ethylene stream is successively compressed and cooled in one or more steps to remove the major part of water, further fed to a fixed bed drying zone and finally to the process of the invention.

In the previous compression steps the recovered water contains a part of the oxygenated contaminants and hydrocarbons dissolved. The contaminated hydrocarbon stream can also be cooled before the first compression step and water recovered. In an embodiment the water recovered upon each cooling further to a compression step and upon cooling, if any, before the first compression step is sent to a stripping column to produce an overhead stream comprising essentially oxygenated contaminants and hydrocarbons and an essentially pure water bottoms stream. Optionally the overhead stream is burned to destroy the oxygenated contaminants and recover heat.

After the compression steps the contaminated ethylene stream is further fed to a fixed bed drying zone and finally to the process of the present invention. The fixed bed drying zone is known in itself.

As regards the stripper, the purpose of said stripper is to recover an overhead comprising essentially H2, CH4 and CO. It is advantageously a distillation column.

As regards the operating conditions, the man skilled in the art of hydrocarbon distillation can select the operating conditions in view of the proportion of light components in the ethylene feed to the stripper and of the thermodynamics properties of the cooling fluids. The basis of the present process is to use mainly propane or propylene to condense the top of the stripper and to "finish" the condensation by cooling with ethane or ethylene to reduce the amount of ethylene which escapes with the light components in the stripper overhead. Advantageously the part of the cooling energy in the second condenser, the one supplied by ethane or ethylene, on top of the stripper is up to 10% of the total cooling energy required on top of the stripper.

The stripper has to be at a pressure high enough to operate at temperatures which are not too low to use mainly liquid propane or liquid propylene as cooling fluid on top. A stripper to recover an overhead comprising H2, CH4 and CO and essentially liquid ethylene at the bottoms operating at 40 barg (4 MPag) has an overhead temperature of around 0 to −10° C. and a bottom temperature of around 0° C. The same stripper operating at 21 barg (2.1 MPag) has an overhead temperature of −30° C. and a bottom temperature of around −24° C. These temperatures and pressures are a function of the proportion of H2, CH4 and CO in the ethylene stream (A) and mainly of the proportion of H2.

As regards to the temperature of stream (D) i.e. the temperature on the top of the stripper and after the first condenser, it ranges from −5° C., −10° C. or −15° C. to −45° C., −40° C. or −35° C. As regard to the temperature of the refrigerant stream of step c) it ranges from −10° C.; −15° C. or −20° C. to −50° C., −45° C. or −40° C. As regards to the temperature liquid ethane or ethylene used in step d), it ranges from −60° C.; −65° C. or −70° C. to −80° C., −85° C. or −90° C.

As regards the first embodiment and the fixed bed CO2 adsorption zone, it can be any component capable to selectively remove CO2. By way of example it is an available commercial fixed bed adsorption (PSA for pressure swing adsorption or TSA for temperature swing adsorption) using molecular sieves or basic oxides, supported basic oxides, high surface area carbons, organo-metallic framework components (MOF's) or mixture thereof. The molecular sieves are preferably low silica zeolites, having 8 (among which zeolite A) or 12 membered (among which zeolite X) rings and exchanged with alkali, alkaline earth or lanthanide cations. Other molecular sieves are crystalline titanosilicates (ETS family materials). Supported basic oxides are preferably, alkali, alkaline earth or lanthanide oxides supported on high surface area carbons, alumina, silica, zirconia or titania, clays. The removal of CO2 can be carried out with a liquid stream or with a gaseous ethylene stream depending on the pressure and temperature. A stream essentially free of CO2 is recovered. As only trace amounts of CO2 have to be removed from the ethylene, the preferred process cycle is of the thermal swing adsorption (TSA) type. Adsorption of CO2 can be performed on two or more fixed bed adsorbent. Said fixed bed adsorbent, once saturated with CO2, can be regenerated, while the main stream is treated on the other adsorption bed or any combination. During regeneration the desorption produces a stream which can be treated anywhere. In a TSA process cycle, the regeneration is done while sweeping the saturated adsorbent with an inert gas by increasing the temperature until desorption of the CO2 occurs. Eventually the saturated adsorbent can be replaced by new adsorbent and the saturated adsorbent either be disposed of or regenerated ex-situ for further use. "Essentially" has to be interpreted in the light of the further use of ethylene. Should ethylene is to be polymerized or oligomerized CO2 has to be 1 ppm vol or less and preferably 0.5 ppm vol or less.

In an embodiment the pressure of the C2 splitter also referred to as a deethanizer is selected to have a temperature of the C2 splitter/deethanizer bottoms such as there is no oligomerization or polymerization of the oxygenates. By way of example said temperature should not exceed 150° C. and advantageously not exceed 100° C. This temperature is function of the pressure and of the proportion of oxygenates in the mixture of oxygenates+ethane+C3+ hydrocarbons. The higher the proportion of oxygenates the higher the temperature. The higher the pressure the higher the temperature is. The C2 splitter/deethanizer is advantageously a distillation column.

Figure 2:
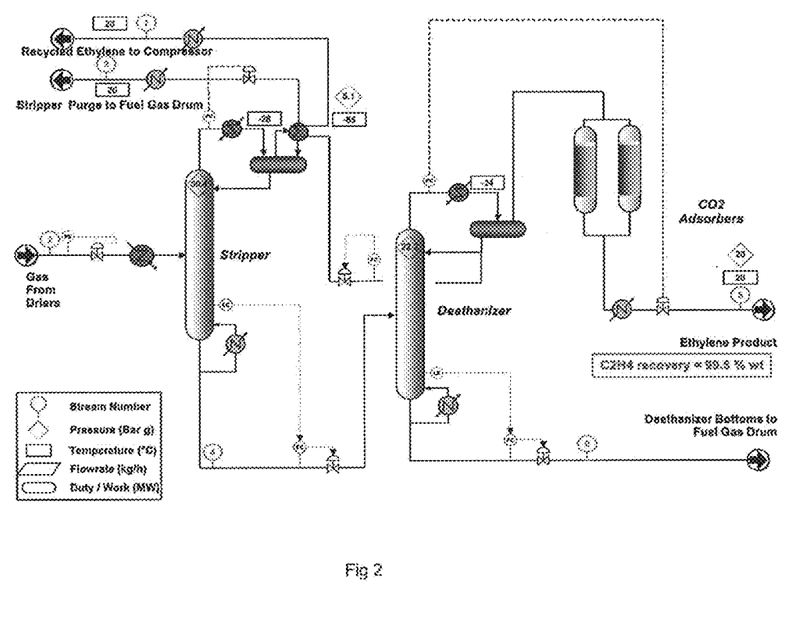
FIG. 2 depicts a flow diagram of a process in accordance with one or more embodiments.

A process according to the first embodiment is described on FIG. 2. The contaminated ethylene stream (A) comprising essentially ethylene, ethane, CO, CO2, H2, CH4, C3+ hydrocarbons and optionally oxygenates has been dried and sent to the stripper (also referred to as a demethanizer) to produce an overhead stream comprising essentially C2H4, CO, H2 and CH4, a bottom stream comprising essentially ethylene, ethane, CO2, C3+ hydrocarbons and optionally oxygenates, said bottom stream of the stripper is sent to the deethanizer to produce a bottom stream comprising essentially ethane, C3+ hydrocarbons and optionally oxygenates, an overhead stream consisting essentially of ethylene and CO2, said overhead of deethanizer is sent to a fixed bed CO2 adsorption zone to recover an ethylene stream essentially free of CO2. A part of liquid ethylene in the reflux drum (also known as decanter) of the deethanizer is expanded and sent as a cooling fluid to condense the first gaseous phase on top of the stripper.

In an embodiment the stripper (demethanizer) and the C2 splitter/deethanizer are operating at the same pressure except the pressure drop between the demethanizer and the C2 splitter/deethanizer for transfer of fluids. Advantageously the pressure is ranging from 15 to 45 barg (1.5 MPag to 4.5 MPag).

In a specific example the pressure of the stripper ranges from 15 to 35 barg (1.5 MPag to 3.5 MPag) and the pressure of the deethanizer and the CO2 adsorbers is about 1 or 2 barg (0.1 MPag to 0.2 MPag) less corresponding to the pressure drop due to pipes and equipment. In this range of pressure the temperature on top of stripper and after the first condenser ranges from −20 to −30° C., the temperature on bottom of stripper ranges from −15 to −25° C., the temperature on top of deethanizer and after the condenser ranges from −30 to −20° C. and the temperature on bottom of deethanizer ranges from 75 to 85° C.

In a specific example the pressure of the stripper ranges from 20 to 25 barg (2.0 MPag to 2.5 MPa) and the pressure of the deethanizer and the CO2 adsorbers is about 1 or 2 barg (0.1 MPag to 0.2 MPag) less corresponding to the pressure drop due to pipes and equipment. In this range of pressure the temperature on top of stripper and after the condenser ranges from −22 to −26° C., the temperature on bottom of stripper ranges from −20 to −24° C., the temperature on top of deethanizer and after the condenser ranges from −27 to −22° C. and the temperature on bottom of deethanizer ranges from 78 to 82° C.

In another specific example the pressure of the stripper ranges from 30 to 45 barg (3.0 MPag to 4.5 MPag) and the pressure of the deethanizer and the CO2 adsorbers is about 5 to 25 barg (0.5 MPag to 2.5 MPag) less. Advantageously the pressure of the deethanizer ranges from 15 to 30 barg (1.5 MPag to 3.0 MPag). In this range of pressure the top of stripper is condensed at a temperature ranging from −20 to −45° C., the temperature on bottom of stripper ranges from −5 to 5° C., the temperature on top of deethanizer ranges from −25 to −35° C., is condensed at a temperature in the range −25 to −35° C. and the temperature on bottom of deethanizer ranges from 75 to 85° C.

Preferably the pressure of the stripper ranges from 25 to 35 barg (2.5 MPag to 3.5 MPag) and the pressure of the deethanizer and the CO2 adsorbers ranges from 20 to 25 barg (2.0 MPag to 2.5 MPag). In this range of pressure the top of stripper is condensed at a temperature ranging from −10 to −35° C., the temperature on bottom of stripper ranges from −5 to −25° C., the temperature on top of deethanizer ranges from −28 to −32° C., is condensed at a temperature in the range −28 to −32° C. and the temperature on bottom of deethanizer ranges from 50 to 80° C.

EXAMPLES

Example 1, According to the Invention

Figure 3:
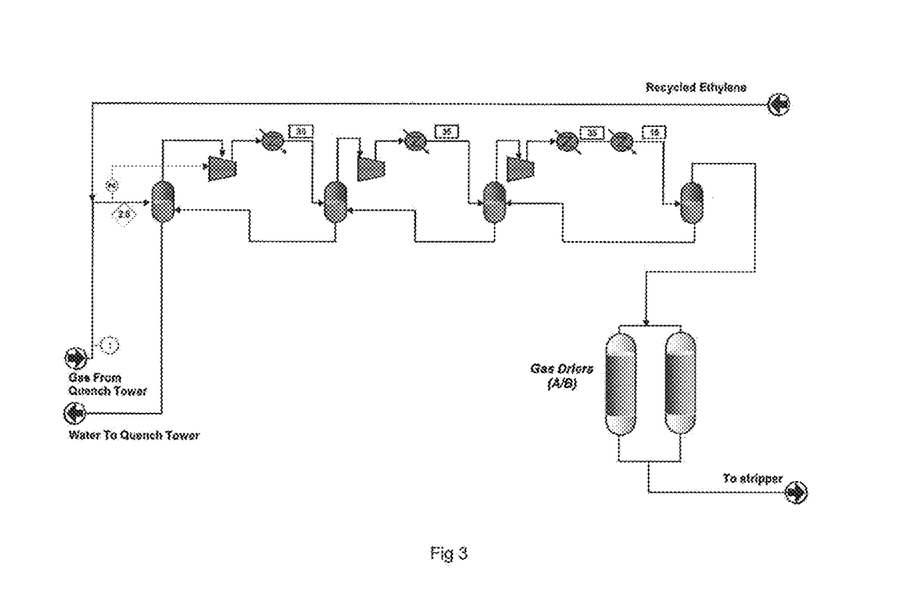
FIG. 3 depicts a flow diagram of a process in accordance with one or more embodiments.

The process according to FIG. 2-3 is operated. The results are on the following table 1:

TABLE 1

| Flowrate kg/h | stream number | | | | | | |
|---|---|---|---|---|---|---|---|
| | 1 | 2 | 3 | 4 | 5 | 6 | 7 |
| H2 | 12 | 12 | 12 | 0 | 0 | 0 | 0 |
| CO | 2 | 2 | 2 | 0 | 0 | 0 | 0 |
| METHANE | 1 | 1 | 1 | 0 | 0 | 0 | 0 |
| ETHYLENE | 25119 | 25954 | 73 | 25881 | 24987 | 59 | 835 |
| ETHANE | 15 | 15 | | 15 | 14 | 0 | 1 |
| CO2 | 8 | 8 | | 8 | 0 | | |
| C3+ | 767 | 720 | | 720 | | 720 | |
| H2O | 197 | | | | | | |
| TOTAL | 26121 | 26712 | 88 | 26624 | 25001 | 779 | 836 |

Stream 1 is the outlet of the quench following the ethanol dehydration, stream 7 is recycled in the compression zone located between the quench and the stripper as shown on FIG. 3.

25119 kg C2H4 are produced, 73 kg are lost in stream 3 and 59 kg are lost in stream 6 which means about 0.5% are lost.

Example 2, Comparative

Figure 4:
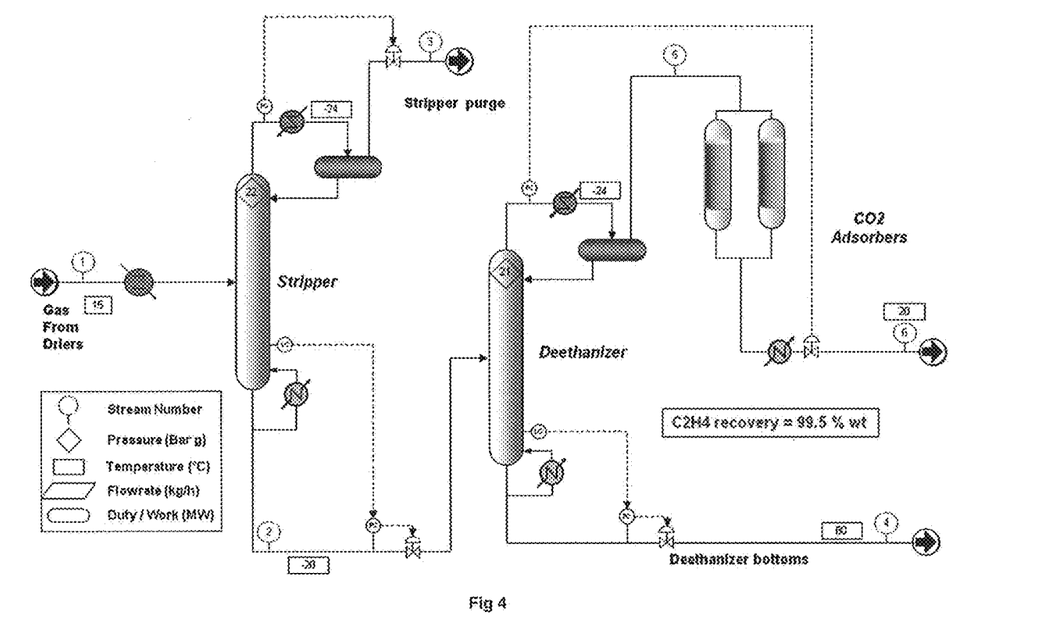
FIG. 4 depicts a flow diagram of a process in accordance with one or more embodiments.

The process according to FIG. 4 is operated. The results are on the following table 2.

TABLE 2

| | | stream No on FIG. 4 | | |
|---|---|---|---|---|
| | | 1 Stripper feed | 2 Stripper bottoms | 3 Stripper purge |
| Temperature | °C. | 15 | −20 | −24 |
| Pressure | bar g | 22 | 22 | 22 |
| H2 | kg/h | 0.1 | | 0.1 |
| CO | kg/h | 1 | | 1 |
| CO2 | kg/h | 1 | 1 | |
| ethane | kg/h | 5 | 5 | |
| ethylene | kg/h | 25091 | 25013 | 78 |
| acetaldehydes | kg/h | 18 | 18 | |
| C3+ | kg/h | 325 | 325 | |
| Total | kg/h | 25441.1 | 25362 | 79.1 |

| | | stream No on FIG. 4 | | |
|---|---|---|---|---|
| | | 4 Deethanizer bottoms | 5 Deethanizer vapor distillate | 6 Ethylene product |
| Temperature | °C. | 80 | −24 | 20 |
| Pressure | bar g | 21 | 21 | 20 |
| H2 | kg/h | | | |
| CO | kg/h | | | |
| CO2 | kg/h | | 1 | |
| ethane | kg/h | | 5 | 5 |
| ethylene | kg/h | 18 | 24995 | 24995 |
| acetaldehydes | kg/h | 18 | | |
| C3+ | kg/h | 325 | | |
| Total | kg/h | 361 | 25001 | 25000 |

By comparison with ex 1 there are much less light components in the stripper feed, as a consequence a condenser cooling at −24° C. is enough. To get −24° C. on the process side the cooling fluid can be liquid propane at 0.5 barg. The C2H4 loss at the stripper overhead is 78 kg/h. In ex 1 to have a C2H4 loss of 73 kg/h at the stripper overhead a second condenser fed with liquid ethylene at −65° C. is required.

25091 kg C2H4 are produced, 78 kg are lost in stream 3 and 18 kg are lost in stream 4 which means about 0.5% are lost.

The invention claimed is:

1. A process for removing light components from an ethylene stream comprising:
    a) providing a dried ethylene stream (A) comprising ethylene, ethane, CO, $CO_2$, $H_2$, $CH_4$, $C_{3+}$ hydrocarbons and optionally oxygenates;
    b) separating said dried ethylene stream (A) in a separation means that is a demethanizer or a stripper to form:
        an overhead gaseous stream (B) comprising ethylene, CO, $H_2$ and $CH_4$; and
        a bottom stream (C) comprising ethylene, ethane, $CO_2$, $C_{3+}$ hydrocarbons and optionally oxygenates;
    c) cooling the overhead gaseous stream (B) to a temperature ranging from −10° C. to −45° C. to form a first gaseous stream (D) and a first liquid stream (E), wherein the cooling is performed with a refrigerant stream that comprises a mixture of liquid and optionally $C_3$ to $C_4$ gaseous hydrocarbons in a first condenser;
    d) further cooling the first gaseous stream (D) to a temperature ranging from −10° C. to −45° C. lower than the temperature of step c) to get a second gaseous stream (F) comprising ethylene CO, $H_2$ and $CH_4$ and a second liquid stream (G), wherein the cooling is performed with liquid ethane or liquid ethylene in a second condenser, wherein the liquid ethane or the liquid ethylene has a pressure ranging from 30 kPag to 500 kPag;
    e) sending the first and second liquid streams (E) and (G) to the separation means as a reflux and;
    either
    i)
    f) sending said bottom stream of step b) to a deethanizer to produce:
        a bottom stream comprising ethane, $C_{3+}$ hydrocarbons and optionally oxygenates; and
        an overhead stream consisting of ethylene and $CO_2$, wherein a portion of a liquid ethylene in a reflux drum of the deethanizer is expanded and used for the cooling in (d); and
    d) sending said overhead of step f) to a fixed bed $CO_2$ adsorption zone to recover an ethylene stream free of $CO_2$;
    or
    (ii)
        f1) sending said bottom stream of step b) to a fixed bed $CO_2$ adsorption zone to recover a stream free of $CO_2$, then sending said stream free of $CO_2$ to a deethanizer to produce:
            a bottom stream comprising ethane, $C_{3+}$ hydrocarbons and optionally oxygenates; and
            an overhead stream consisting of ethylene free of $CO_2$.

2. The process according to claim 1, wherein the refrigerant stream comprises liquid and optionally gaseous propane and/or liquid and optionally gaseous propylene, wherein the liquid propane or the liquid propylene has a pressure ranging from 30 kPag to 200 kPag.

3. The process according to claim 1, wherein during the cooling of the first gaseous stream (D) the liquid ethylene in step (d) returns to gas phase and is recycled.

* * * * *